(12) United States Patent
Ozawa et al.

(10) Patent No.: US 8,690,838 B2
(45) Date of Patent: Apr. 8, 2014

(54) TRANSDERMAL ADMINISTRATION DEVICE

(75) Inventors: Hiroshi Ozawa, Haibara-gun (JP);
Kiyoshi Ishibashi, Haibara-gun (JP);
Akinori Inou, Haibara-gun (JP);
Masahiro Takigawa, Kyoto (JP)

(73) Assignee: Nanbu Plastics Co., Ltd., Shizuoka (JP)

( * ) Notice: Subject to any disclaimer, the term of this patent is extended or adjusted under 35 U.S.C. 154(b) by 15 days.

(21) Appl. No.: 13/318,319

(22) PCT Filed: Apr. 30, 2010

(86) PCT No.: PCT/JP2010/058071
§ 371 (c)(1),
(2), (4) Date: Jan. 17, 2012

(87) PCT Pub. No.: WO2010/126174
PCT Pub. Date: Nov. 4, 2010

(65) Prior Publication Data
US 2012/0109067 A1    May 3, 2012

(30) Foreign Application Priority Data

May 1, 2009 (JP) ................................ 2009-112255
Apr. 23, 2010 (JP) ................................ 2010-100320

(51) Int. Cl.
*A61M 25/00* (2006.01)
*A61B 17/20* (2006.01)
*A61M 37/00* (2006.01)

(52) U.S. Cl.
USPC .......................................... 604/264; 604/46

(58) Field of Classification Search
USPC ............. 604/46, 48, 264, 263, 173, 194, 229, 604/68–70, 132–139, 383
See application file for complete search history.

(56) References Cited

U.S. PATENT DOCUMENTS

| | | | |
|---|---|---|---|
| 3,964,482 A | 6/1976 | Gerstel et al. ................. | 128/260 |
| 6,743,211 B1 | 6/2004 | Prausnitz et al. | |
| 7,422,567 B2 | 9/2008 | Lastovich et al. ............... | 604/46 |
| 2005/0027255 A1 | 2/2005 | Lavi et al. ..................... | 604/135 |
| 2005/0096586 A1 | 5/2005 | Trautman et al. | |
| 2006/0253078 A1 | 11/2006 | Wu et al. ....................... | 604/173 |
| 2007/0270738 A1* | 11/2007 | Wu et al. ......................... | 604/46 |
| 2010/0137810 A1* | 6/2010 | Chandrasekaran et al. .. | 604/198 |

FOREIGN PATENT DOCUMENTS

| | | |
|---|---|---|
| JP | 2005-537056 A | 12/2005 |
| JP | 2006-149818 A | 6/2006 |
| JP | 2007-500530 A | 1/2007 |
| JP | 2007-037885 A | 2/2007 |
| JP | 2008-79919 A | 4/2008 |

(Continued)

*Primary Examiner* — Jason Flick
*Assistant Examiner* — Rebecca E Eisenberg
(74) *Attorney, Agent, or Firm* — Seed IP Law Group PLLC

(57) ABSTRACT

The transdermal administration device of the present invention includes: a needle support with a plurality of microneedles formed at a tip portion thereof; a holder with the needle support placed therein, allowing the needle support to protrude itself therefrom and retract therein; and a cap for covering the microneedles, and further includes: a spring member placed between the needle support and the holder, for biasing the needle support in a protruding direction; an engaging portion at a base of the needle support; and an engaged portion capable of engaging the engaging portion, formed in the holder, where the engaging portion of the needle support can be locked with the engaged portion of the holder when the needle support is retracted in the holder.

11 Claims, 8 Drawing Sheets

(56) References Cited

FOREIGN PATENT DOCUMENTS

| | | |
|---|---|---|
| JP | 2008-539010 A | 11/2008 |
| KR | 10-0802155 B1 | 2/2008 |
| WO | WO2004/020034 A2 | 3/2004 |
| WO | WO2005/009515 A1 | 2/2005 |
| WO | WO2006/116281 A2 | 11/2006 |
| WO | WO 2008/101892 A1 | 8/2008 |
| WO | WO2009/130926 A1 | 10/2009 |

* cited by examiner

12

TRANSDERMAL ADMINISTRATION DEVICE

TECHNICAL FIELD

The present invention relates to a transdermal administration device for transdermally administering a medical fluid, and more particularly, to a disposable type of transdermal administration device.

BACKGROUND ART

A syringe is conventionally used for administering a medical fluid or a medicine (referred to as a medical fluid, hereinafter) that cannot be administered orally. However, a method using a syringe provides a large degree of stress and pain to a patient. Another method is also used for transdermal administration by using a medical patch which contains a medical fluid; however, this method has a problem of requiring an extended period of time until the medicine takes effect and of limiting the kind of medical fluids usable.

In order to solve the problems mentioned above, medical fluid administration techniques have been developed involving microneedles and microblades.

A medical fluid administering method using a microneedle (Japanese Laid-Open Publication No. 2006-149818, Reference 1) is used for the purpose of reducing the time until the effect of the medicine appears by administering a medical fluid directly to a live cell layer (epidermis below the prickle cell layer) of the cuticle. The method is also used for the purpose of reducing the time until the effect of the medicine, such as insulin or an anesthetic, appears and a time until the effect of a physiological active substance, such as DNA, RNA, protein and peptide, appears, with a similar principle.

The microneedle is a microscopic needle with generally a tip of 10 μm in diameter, 100 μm in height, and with a base of 100 μm in diameter. The microneedle is a micro structure with a large aspect ratio. Therefore the medical fluid administering method using a microneedle has the advantage of not causing pain upon inserting it into a human body because the microneedle does not reach a pain spot since it only penetrates the stratum corneum of the skin.

CITATION LIST

Patent Literature

[PLT1]
Japanese Laid-Open Publication No. 2006-149818

SUMMARY OF INVENTION

Technical Problem

A problem with using a device that has a conventional microneedle is that the device may require a large amount of medical fluid to reach the microneedle. That is, the reservoir housing the medical fluid is provided in the device, and the medical fluid is delivered from the medical fluid reservoir to the microneedle. Thus, it is necessary to fill the reservoir with a large amount of the medical fluid in order for the medical fluid to reach the vicinity of the microneedle.

Furthermore, since the device using a conventional microneedle is structured to be usable after an administration of medical fluid, there is a possibility that the used device is mistakenly used by a number of people.

The present invention is intended to solve the conventional problems described above. An objective of the present invention is to provide a transdermal administration device capable of reliable transdermal administration with small amounts of medical fluid.

Another objective of the present invention is to provide a disposable transdermal administration device that cannot be mistakenly used by more than one subject.

The present invention is characterized as follows in order to solve the problems described above.

A transdermal administration device includes: a needle support with a plurality of microneedles formed at a tip portion thereof; a holder with the needle support placed therein, allowing the needle support to protrude itself therefrom and retract itself therein; and a cap for covering the microneedles, the transdermal administration device further including: a spring member placed between the needle support and the holder, for biasing the needle support in a protruding direction; an engaging portion formed at a base of the needle support; and an engaged portion formed in the holder, capable of engaging the engaging portion, where the engaging portion of the needle support can be engaged with the engaged portion of the holder when the needle support is retracted in the holder.

Preferably, in the transdermal administration device according to the present invention, the engaging portion formed at the base of the needle support is a protruded portion, the engaged portion formed in the holder is a through hole, and the protruded portion is engaged with the through hole.

Still preferably, in the transdermal administration device according to the present invention, the base of the needle support includes an elastic piece being extended therefrom, and the protruded portion is formed on an outer surface of the elastic piece.

Still preferably, in the transdermal administration device according to the present invention, the cap includes a retaining portion placed inside the cap, the retaining portion capable of retaining a medical fluid.

Still preferably, in the transdermal administration device according to the present invention, the cap includes a seal portion formed in a wall portion of the cap, the seal portion allowing a needle for providing the medical fluid to be inserted, and the needle penetrating through the seal portion can provide the medical fluid in the retaining portion.

Still preferably, in the transdermal administration device according to the present invention, the needle support includes therein a medical fluid retaining portion provided with a medical fluid, and the medical fluid retaining portion is continuously connected with a surface of the tip portion of the needle support through a fluid passage hole.

Still preferably, in the transdermal administration device according to the present invention, the transdermal administration device is formed of biodegradable plastic.

Still preferably, in the transdermal administration device according to the present invention, the microneedle is formed of thermoplastic resin or metal, having a base diameter of Φ10 to 1000 μm, a tip diameter 10 to 1000 μm, and a height of 10 to 1500 μm.

Still preferably, in the transdermal administration device according to the present invention, the tip portion of the needle support is formed to be a planar or convex surface, and the plurality of microneedles are formed at the tip portion.

A transdermal administration device includes: a needle support with a microneedle provided at a tip portion thereof; a holder for holding the needle support movably; and a cap attached to the tip portion of the needle support to cover the microneedle, in which a medical fluid storing portion is formed at a tip portion of the needle support, the medical fluid storing portion being continuously connected to the microneedle; a spring for biasing the needle support in a protruding direction is placed between the needle support and the holder; and a plunger for sealing an opening of the medical fluid storing portion is placed between the needle support and the holder, with a space being formed between the plunger and the holder.

Advantageous Effects of Invention

According to the present invention, the following effects can be achieved.

The transdermal administration device according to the present invention has the following structure: The spring member for biasing the needle support in the protruding direction is located between the needle support and the holder. The engaging portion is formed at the base of the needle support, and the engaged portion capable of engaging with the engaging portion is formed on the holder. The engaging portion of the needle support can be locked with the engaged portion of the holder when the needle support is retracted in the holder.

Accordingly, the adhesion of the medical fluid onto the microneedles at the tip portion of the needle support and the pressing of the needle support against a skin allow the microneedles to pierce the skin. At the same time, owing to the pressing force, the needle support is retracted in the holder, and the engaging portion of the needle support is locked with the engaged portion of the holder. As a result, once the transdermal administration device according to the present invention is used, the needle support is retracted in the holder, which state clearly indicates that the transdermal administration device has been used.

In addition, the transdermal administration device can be used by adhering the medical fluid onto the tip portion of the needle support, so that a medical fluid reservoir need not be provided in the device unlike the conventional device, making it possible to reduce the amount of the medical fluid consumed.

DESCRIPTION OF EMBODIMENTS

Hereinafter, embodiments of the present invention will be described with reference to the accompanying figures.

Figure 1:
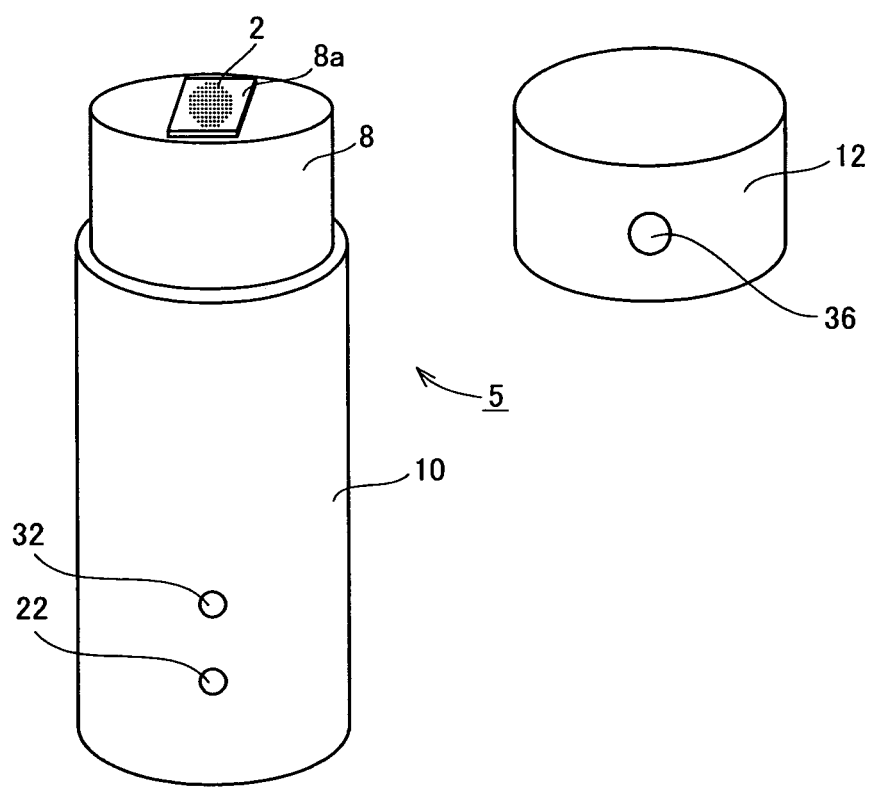
FIG. 1 is an exploded perspective view of a transdermal administration device.

As illustrated in FIG. 1, a transdermal administration device 5 according to the present invention includes: a needle support 8 with a plurality of microneedles 2 formed on a tip portion thereof; a cylindrical holder 10 with the needle support 8 placed therein, allowing the needle support 8 to protrude therefrom and retract therein; and a cap 12 attached to the holder 10 to cover microneedles 2.

The needle support 8 is formed substantially cylindrical, and its tip portion 8a is formed as a planar or convex surface. The plurality of microneedles 2 are placed on the tip portion 8a.

Figure 11:
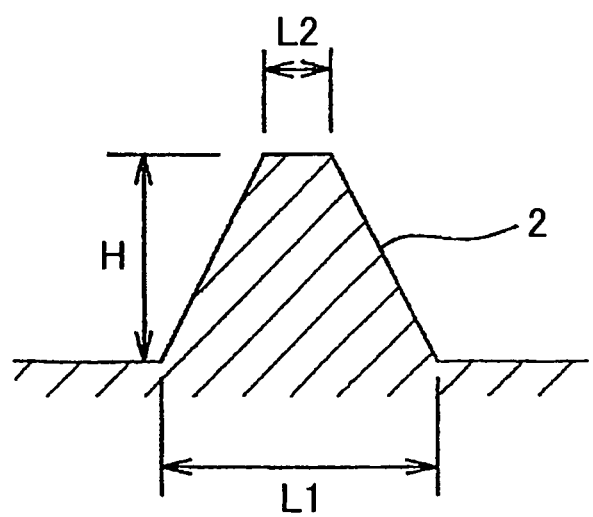
FIG. 11 is an enlarged cross sectional view of a microneedle.

As illustrated in FIG. 11, each microneedle 2 is formed in a shape of a truncated cone, and is formed such that a base diameter L1 is $\Phi$10 to 1000 μm (preferably 50 to 300 μm), a tip diameter L2 of the needle is 10 to 1000 μm, and the length (height) H is 10 to 1500 μm (preferably 300 to 1000 μm).

In addition, the tip portion 8a of the needle support 8 is provided with 1 to about 10000 of the microneedles 2 having a pitch of 0.1 to 20 mm.

Figure 2:
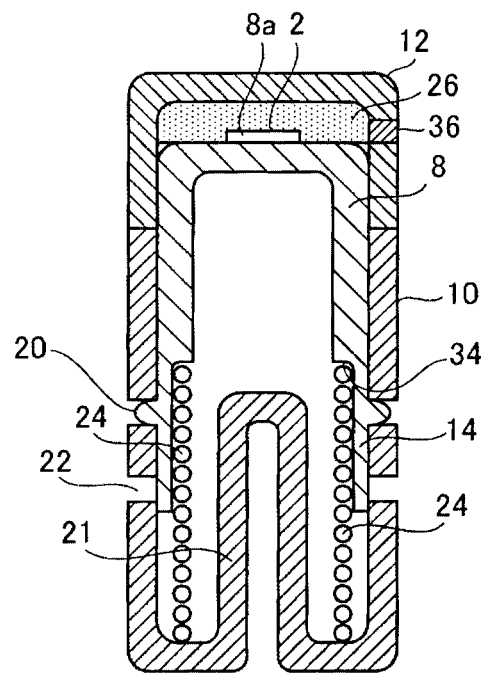
FIG. 2 is a cross sectional view of a transdermal administration device.
Figure 3:
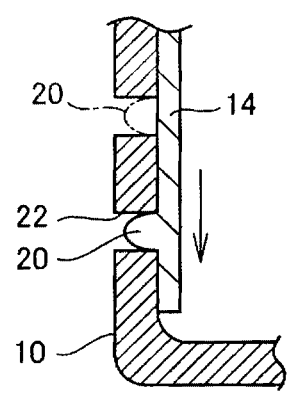
FIG. 3 is an enlarged cross sectional view of a part of a transdermal administration device.
Figure 3:
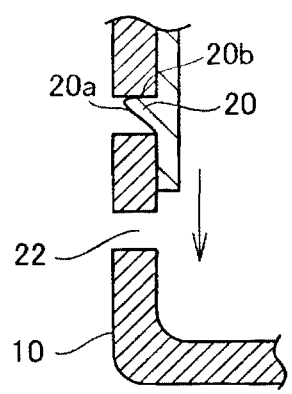
Figure 4:
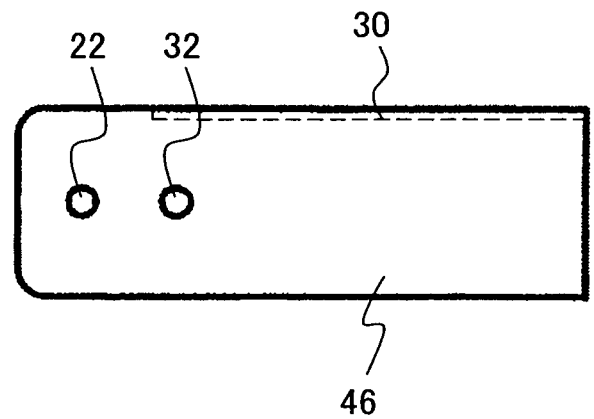
FIG. 4 is an elevation view of a holder.
Figure 5:
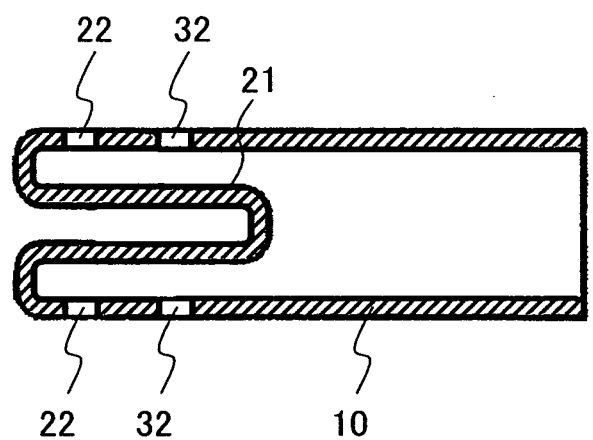
FIG. 5 is a cross sectional view of a holder.
Figure 6:
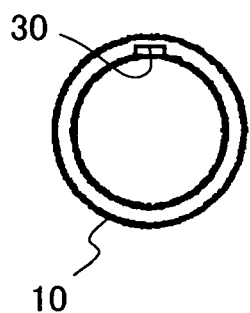
FIG. 6 is a plan view of a holder.
Figure 7:
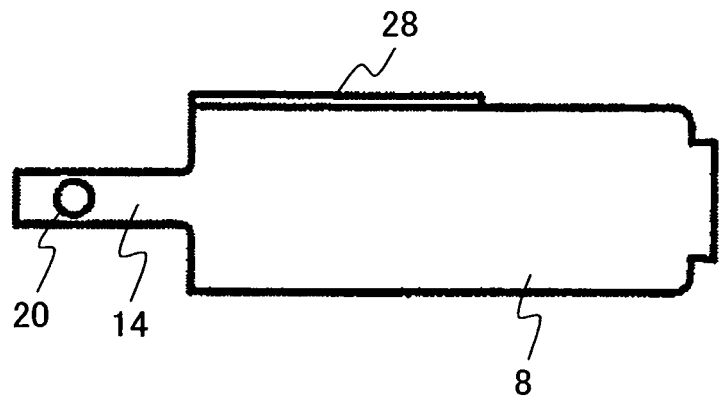
FIG. 7 is an elevation view of a needle support.
Figure 8:
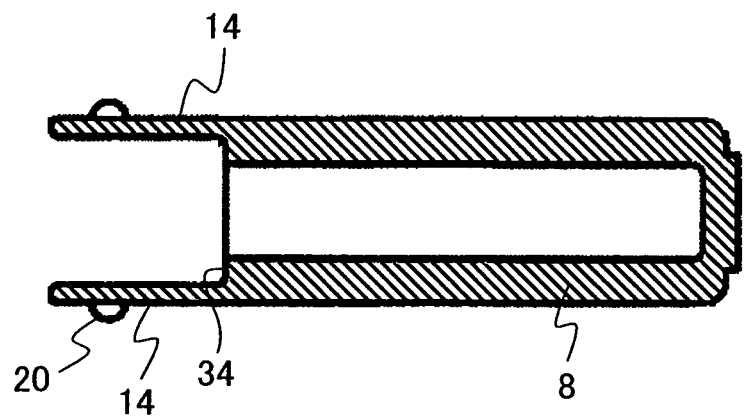
FIG. 8 is a cross sectional view of a needle support.
Figure 9:
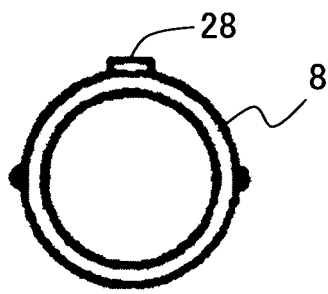
FIG. 9 is a plan view of a needle support.
Figure 10:
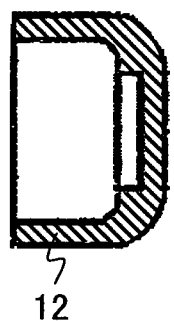
FIG. 10 is a cross sectional view of a cap.

As illustrated in FIGS. 2 and 7, the base of the needle support 8 includes two elastic pieces 14 monolithically extended therefrom. The two elastic pieces 14 and 14 are provided at the base of the needle support 8, being placed opposite one another. The elastic pieces 14 can elastically change their form slightly in the radius direction of the needle support 8. An engaging portion 20 is protrudingly formed on an outer surface of each elastic piece 14. The engaging portion 20 can be formed with a semicircle-shaped protruded portion, or alternatively it can be formed, as illustrated in FIG. 3(b), with a protruded portion 20 having a slanting surface 20a and a locking surface 20b. In addition, a guide portion 28 is protrudingly formed on the outer surface of the needle support 8, running along the axis direction.

The holder 10 is formed cylindrical and houses the needle support 8, allowing the support to protrude and retract itself. The inside diameter of the holder 10 is formed slightly larger than the external diameter of the needle support 8. The inner surface of the holder 10 includes a concave groove 30 formed therein and running in the longitudinal direction. The concave groove 30 is formed such that a guide portion 28 of the needle support 8 is inserted in the concave groove 30 so that the needle support 8 can stably move within the holder 10 without lateral movement.

A through hole 22 is formed as the engaged portion at the base of the holder 10. The through hole 22 is formed at two opposing portions in the holder 10. In addition, a second through hole 32 is formed at the base of the holder 10 in an adjacent position of the through hole 22.

When the needle support 8 is inserted in the holder 10, the elastic pieces 14 are elastically changed and the protruded portion 20 is engaged with the through hole 22. In such a state, the tip of the protruded portion 20 does not protrude out from the outer surface of the holder 10 because the protruding size of the protruded portion 20 is smaller than the width of the holder's wall.

A center protrusion 21 for retaining a coil spring 24 is provided at the base of the holder 10.

A step portion 34 is formed at the base of the needle support 8, and the elastic pieces 14 extended from the step portion 34, in such a manner as described above. In addition, a compressed state of the spring 24 is placed between the step portion 34 and the bottom portion of the holder 10.

Accordingly, in a state where the needle support 8 is inserted in the holder 10 and the protruded portion 20 is engaged in the second through hole 32 of the holder 10, the needle support 8 is biased in the protruding direction by the spring 24.

The through hole 22 may be formed as a blind hole without breaking through to the outer side. Alternatively, the engaged portion may be formed with a protrusion formed within the holder 10. Further, it is not necessary to form the second through hole 32. In such a case, the needle support 8 is supported in the holder 10 by the spring 24.

The cap 12 is attached to the holder 10, covering the microneedles 2 and the needle support 8. The cap 12 may also be watertightly attached to the holder 10 with a screw, or may also be watertightly attached to the holder 10 with a rubber ring interposed therebetween.

A retaining portion 26, which can retain a medical fluid, is placed inside the cap 12. Publicly known material with characteristics capable of absorbing and retaining a medical fluid can be used as the retaining portion 26, which material includes cotton, woven cloth, nonwoven cloth, sponge and the like.

In addition, a seal portion 36 is formed in a wall portion of the cap 12. The seal portion 36 allows the insertion of a needle for providing a medical fluid. That is, a hole portion is formed in the wall portion of the cap 12, and an elastic material, such as silicon rubber, is filled. Thereby, it is possible to insert a needle of a medical fluid providing device through the seal portion 36 to provide the medical fluid for the retaining portion 26 while maintaining its airtight state.

Thermoplastic resins, such as polycarbonate, polypropylene, ABS resin and polystyrene, can be used as the material of the above needle support 8, holder 10, and cap 12, and they are manufactured through injection molding, imprint molding or the like. In particular, they can be manufactured with biodegradable plastics such as polylactic acid. In addition, the needle portion only may be formed with metal.

As illustrated in FIG. 1, the surface of the tip portion 8a of the needle support 8 is planar or convex in shape. The tip portion 8a may be formed on a circular or quadrilateral member of 1 to 10 mm in diameter or one side 1 to 10 mm in length. The plurality of microneedles 2 are assembled and placed at the tip portion 8a. In the case where the tip portion 8a is formed to be convex, the radius of curvature R thereof is preferably 2 to 100 mm, and more preferably 10 to 40 mm, and still more preferably 30 to 40 mm.

For a metal mold for forming the microneedles, a large number of holes of micron order need to be made. Thus the metal mold is preferably manufactured through cutting with a micron bite, casting with a punching tool, electrodischarge machining, etching, electroforming, or the like.

Next, a method for using the transdermal administration device 5 according to the present invention will be described.

The stratum corneum where a medical fluid is to be administrated is peeled off the skin as much as possible in advance. The stratum corneum is constantly peeled off naturally as grime, and a new stratum corneum is produced. It is therefore easy to peel off this portion artificially, and the peeling does not cause pain. The thickness of the stratum corneum is 10 to 20 μm, and the thickness varies more or less depending on the age, sex and the like. The same applies to the elasticity of the stratum corneum. For example, an adhesive tape is adhered on the skin and is peeled off the skin, thus removing the stratum corneum.

Meanwhile, the needle of the medical fluid providing device is penetrated through the seal portion 36 of the cap 12 to provide the medical fluid for the retaining portion 26. Thereby, the medical fluid is adhered to the microneedles 2, which are formed at the tip portion 8a of the needle support 8.

Next, the cap 12 is removed from the holder 10. Since the tip portion 8a of the needle support 8 is protruded outside from the holder 10, the tip portion 8a is pressed against the skin (pressed against the portion of the skin where the stratum corneum has been peeled off). The microneedles 2 are penetrated into the skin, and the medical fluid is provided in the live cell layer (epidermis below the prickle cell layer) of the cuticle. Simultaneously, owing to the pressing force, the needle support 8 is retracted back in the holder 10, resisting the elastic material 24. As a result, the engaging portion 20 is engaged with the through hole 22. The outer surface of the engaging portion 20 cannot protrude outside from the through hole 22, so that the tip of the engaging portion 20 cannot be pressed for operation by a human's finger or the like. As a result, the needle support 8 is retracted in the holder 10, allowing the user to clearly see from the outside that the needle support 8 has been used.

According to the method for administration described above, the thickness of the skin becomes thinner based on the thickness of the stratum corneum that is peeled off the skin. Accordingly, by adjusting the height of the microneedles 2 to 10 to 1500 μm, all or almost all of the microneedles result in reaching a live cell layer (epidermis below the prickle cell layer) of the skin. At the tip portion 8a of the needle support 8, 1 to 10000 of the microneedles 2 are provided having a pitch of 0.1 to 20 mm, thereby effectively providing the medical fluid into the live cell layer (epidermis below the prickle cell layer) of the skin.

In addition, since the length of the microneedles 2 can be maintained short, a sufficient degree of strength can be maintained for the microneedles 2 specifically with the base diameter of Φ10 to 1000 μm (preferably 50 to 300 μm) and the tip diameter of Φ10 to 1000 μm, without the necessity of forming thick microneedles 2. Thus thereby prevents the microneedles 2 from snapping or breaking in the body during the administering of the medical fluid, and avoiding the microneedles 2 from being left in the body before it happens.

In the case where the surface of the needle support 8 is formed in a convex shape, when the needle support 8 is pressed against the skin, the tip portion 8a is concentratedly pressed hard and the pressure is not spread. As a result, almost all the microneedles 2 are inserted into the skin, thereby effectively providing the medical fluid in the skin.

By forming the tip portion 8a of the needle support 8 in a convex shape (with the radius of curvature of R 12 to 100 mm, and preferably 30 to 40 mm), all or a part of the microneedles enter the skin uniformly without unevenness when the tip portion is pressed against the skin of a human. This provides a suitable efficiency of transdermal administration.

As a result, it becomes possible to reduce the time until the effect of medicine, such as insulin and an anesthetic, appears and the time until the effect of a physiological active substance, such as DNA, RNA, protein and peptide, appears.

Furthermore, the peeling of the stratum corneum does not cause pain and the microneedles 2 do not reach the pain spot, so that the burden of a patient can be extremely light.

The needle support 8 may be in the shape of a square, a rectangular, an ellipse or the like, other than a circular shape. In addition, the surface of the tip portion 8a, which is a surface contacting the skin, is not limited to a convex shape, but may be a planar shape. In addition, the shape of the microneedles 2 is not limited to the one described above.

The microneedles 2 are formed of thermoplastic resin or metal, and are formed to have a base diameter of Φ10 to 1000 μm (preferably 50 to 300 μm), a tip diameter of Φ10 to 1000 μm, and the length (height) of 10 to 1500 μm (preferably 300 to 1000 μm). As a result, the microneedles 2 have a sufficient strength to be inserted into the live cell layer (epidermis below the prickle cell layer) of the cuticle, where as much stratum corneum as possible is peeled off. Further, the microneedles 2 have the height of 10 to 1500 μm (preferably 300 to 1000 μm), so that the medical fluid can be reached in the skin in a short period of time.

The portion where the microneedles are assembled is provided with 1 to 10000 of the microneedles 2 at 0.1 to 20 mm pitch, so that the medical fluid can be provided effectively to the live cell layer (epidermis below the prickle cell layer) of the cuticle.

In the above embodiment, the retaining portion 26 for retaining the medical fluid is provided for the cap 12; however, a medical fluid retaining portion, for which the medical fluid is provided, may be placed in the needle support 8. The medical fluid retaining portion is continuously connected with the tip portion 8a of the needle support 8 through a fluid passage hole for the medical fluid. The position of the fluid passage hole is not limited to the center of the tip portion 8a of the needle support 8, but the fluid passage hole may be provided in the periphery of the tip portion 8a or in the convex surface.

Figure 12:
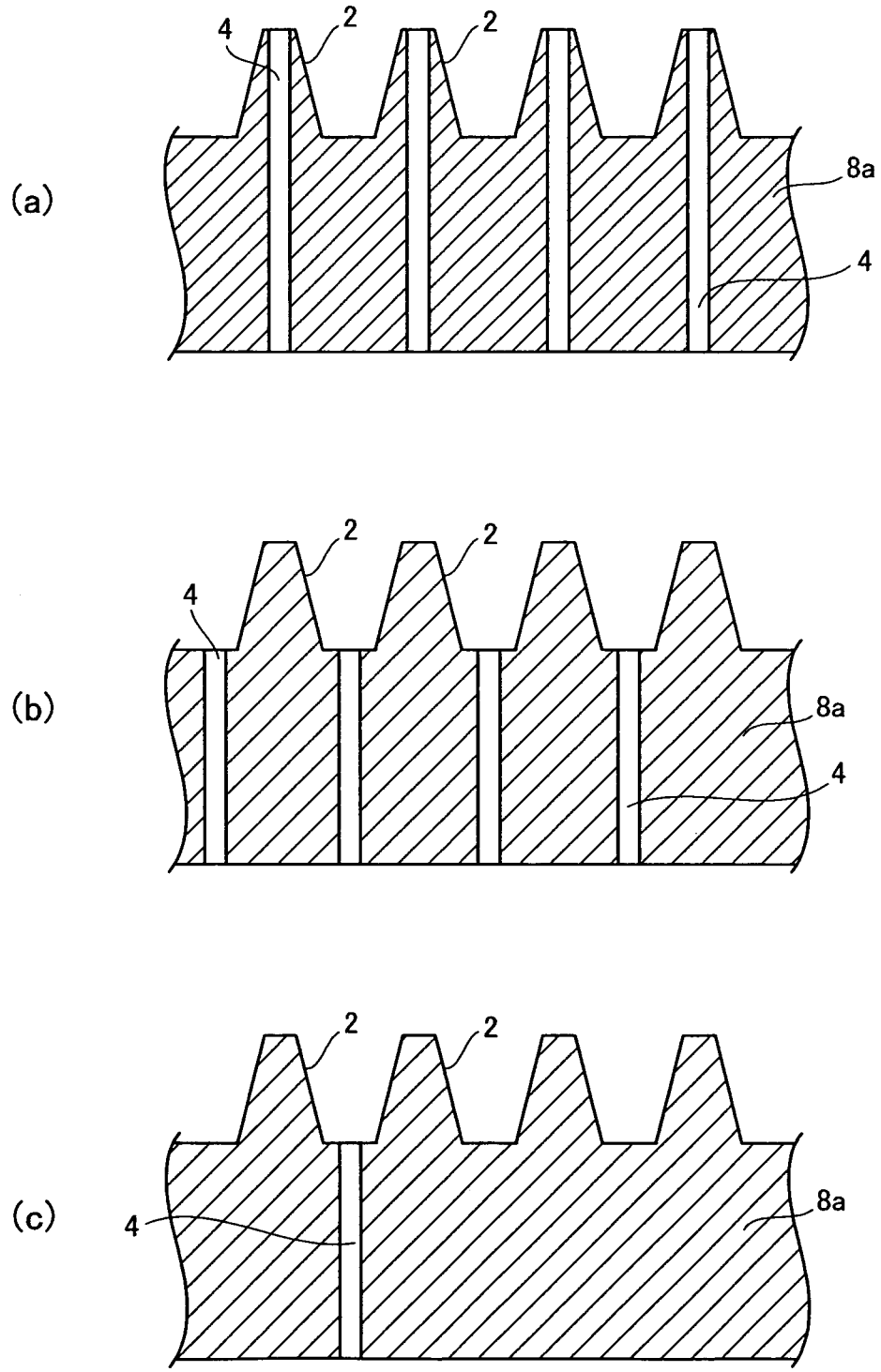
FIG. 12 is an enlarged cross sectional view of a microneedle according to another embodiment.

As illustrated in FIG. 12(a), the fluid passage hole 4 may also be formed in such a manner to pass through the microneedle 2. Alternatively, as illustrated in FIG. 12(b), the fluid passage hole 4 may also be formed in such a manner to pass through, not the microneedle 2, but the tip portion. In the case where the fluid passage hole 4 passes through the microneedle 2, it may pass through the tip portion of the microneedle 2. Alternatively, the fluid passage hole 4 may be formed at a position offset from the tip portion of the microneedle 2. That is, the fluid passage hole 4 may be formed in such a manner that the fluid passage hole 4 passes through a slanting surface of the microneedle 2. As illustrated in FIG. 12(c), one fluid passage hole 4 may be formed, or two or more of the fluid passage holes 4 may be formed.

Further, the microneedle (needle portion) is not limited to be formed in the circular cone shape, but may be formed in a triangular pyramid, a quadrangular pyramid or the like. Further, a groove for passing the administered medical fluid may be formed in the height direction. Further, a fluid passage hole may be provided from the vicinity of the tip of the needle portion to the back surface of the tip portion.

A plunger movable in the axis direction is placed in a space portion formed in the needle support 8, and the medical fluid retaining portion is formed between the plunger and the tip portion 8a of the needle support 8. An operation section of the plunger is protruded more than a back end portion of the holder 10. By the operation of the operation section, the plunger is moved in the longitudinal direction of the holder 10, thereby oozing out the medical fluid provided inside the medical fluid retaining portion via the fluid passage hole to the microneedles 2. Thereafter, the microneedles 2 are pressed against the skin as described above.

Figure 13:
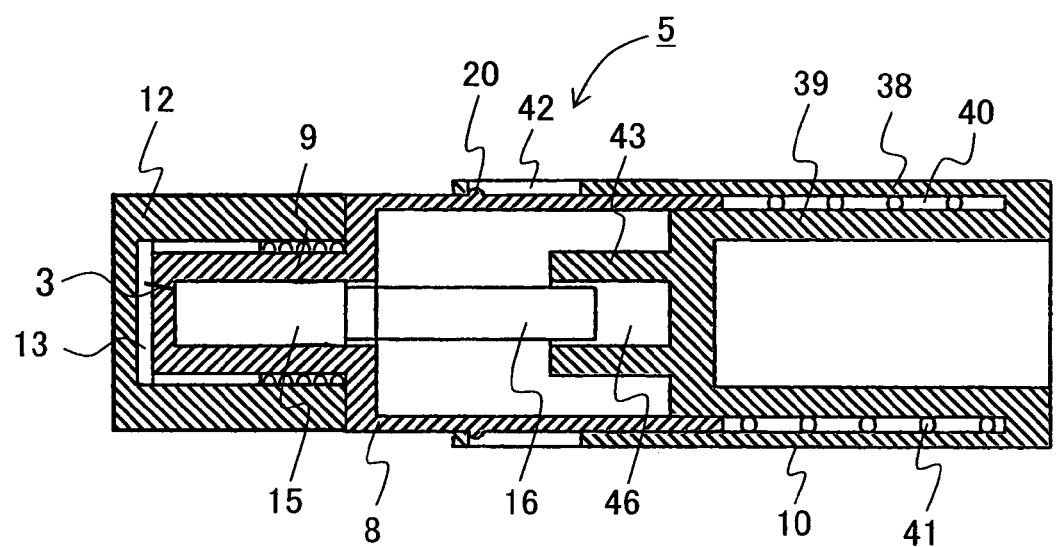
FIG. 13 is a cross sectional view of a transdermal administration device according to another embodiment of the present invention.
Figure 14:
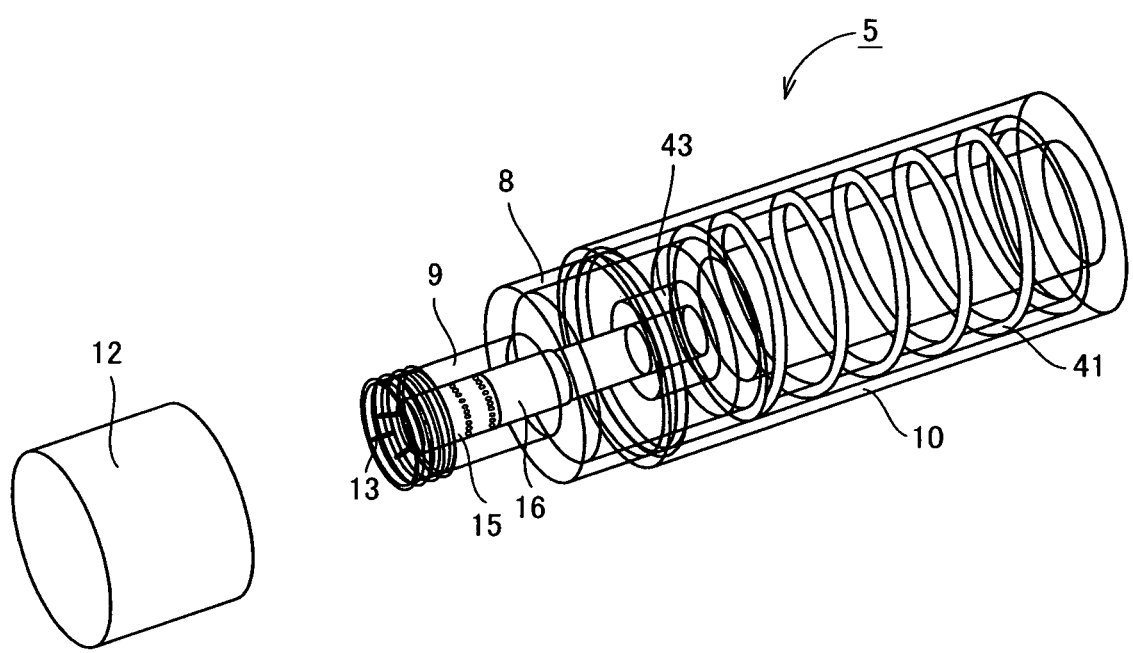
FIG. 14 is a perspective view of the transdermal administration device illustrated in FIG. 13.

FIGS. 13 and 14 further illustrate another embodiment.

A transdermal administration device 5 includes: a needle support 8 with one or a plurality of microneedles 3 formed at a tip portion thereof; a cylindrical holder 10 with the needle support 8 movably inserted therein; and a cap 12 attached to the tip portion of the needle support 8 to cover the microneedles 3.

The needle support 8 is formed substantially cylindrical, and a protruded portion 9 is formed at the tip portion of the needle support 8, the protruded portion 9 having a diameter smaller than that of the main body of the needle support 8. The microneedles 3 are attached to a tip surface of the protruded portion 9.

The microneedles 3 can be made of resin or metal. In the present embodiment, three needles 3 are fixed at the protruded portion 9 and the tip of the needles are protruded outwardly from the surface of the protruded portion 9. The angle of inclination of the microneedles 3 can be from 0 to 10 degrees outwardly in the radius direction. Each angle from the mutual center point of the three needles 3 is set to be 120°. The diameter of the microneedles 3 can be from about 0.1 to 0.5 mm. The microneedles 3 are protruded about 0.1 to 1.5 mm from a surface of the needle support 8.

As described above, the needles 3 may be fixed to the tip portion of the needle support 8 such that the tips of the microneedles 3 point outwardly in the radius direction, or the microneedles 3 may be fixed to the tip portion of the needle support 8 such that the microneedles 3 are parallel to the axis direction of the needle support 8.

A medical fluid storing portion 15 is formed at the tip portion of the needle support 8.

An engaging portion 20 is protrudingly formed on an outer surface of the needle support 8. The engaging portion 20 can be formed of a semicircle protruded portion.

The holder 10 is formed substantially cylindrical, housing the needle support 8 in a movable manner. The holder 10 includes an outer cylinder 38 and an inner cylinder 39, and a base of the outer cylinder 38 is connected to a base of the inner cylinder 39. A ring-shaped space portion 40 is formed between the outer cylinder 38 and the inner cylinder 39. A base of the needle support 8 is inserted in the space portion 40.

A spring 41 is placed in the space portion 40 between the holder 10 and the needle support 8. In a condition where the needle support 8 is inserted in the holder 10, the needle support 8 is biased by the spring 41 in a direction protruding from the holder 10.

A long hole 42 is formed at the tip portion of the outer cylinder 38 of the holder 10, being extended in the axis direction of the holder 10. Two of the long holes 42 are formed at opposing positions of the holder 10.

When the needle support 8 is inserted in the holder 10, the engaging portion 20 of the needle support 8 is inserted in the long hole 42. The needle support 8 is pushed towards its protruding direction by the biasing force of the spring 41. The engaging portion 20 is engaged with an edge portion on one side of the long hole 42.

A ring-shaped protruded portion 43 is formed at a tip portion of the inner cylinder 39 of the holder 10. An end portion on one side of a plunger 16 is inserted in a hole portion 46 of the ring-shaped protruded portion 43. An end portion on the other side of the plunger 16 is inserted in the medical fluid storing portion 15 described above, the tip of the plunger 16 sealing an opening of the medical fluid storing portion 15.

The cap 12 is attached to the tip portion of the needle support 8 in such a manner to cover the needles 3. The cap 12 may be watertightly attached to the needle support 8 with a screw, or may be watertightly attached to the needle support 8 with a rubber ring interposed therebetween.

A rubber-made protection plate 13 is placed inside the cap 12.

Next, a method for using the transdermal administration device 5 will be described.

A medical fluid is supplied beforehand in the medical fluid storing portion 15. The cap 12 is removed from the protruded portion 9 of the needle support 8. The holder 10 is held by the hand, and the protruded portion 9 of the needle support 8 is pressed against the skin.

The pressurizing force to the skin by the holder 10 is transmitted to the needle support 8 through the spring 41, piercing the needles 3 into the skin. By the pressing force of the holder 10, the spring 41 is further compressed, and the ring-shaped protruded portion 43 of the holder 10 moves the plunger 16 towards the tip direction of the plunger 16. The plunger 16 is inserted in the medical fluid storing portion 15. As a result, the medical fluid is pressurized in the medical fluid storing portion 15 and is administered into the skin through the needles 3. When almost all the medical fluid is pushed out of the medical fluid storing portion 15 and then the pressing force to the holder 10 is released, the holder 10 is returned back to its original position by the elastic force of the spring 41.

According to the above administration method, the medical fluid is administered into the skin slightly after the needles 3 are inserted in the skin, thereby securely administering the medical fluid in the skin.

The device according to the present invention can also be used as a device for reducing wrinkles. In such a case, medical fluids, such as collagen, Botox or the like, can be used. Further, in such a case, the microneedles are applied directly to the skin with or without the peeling off of the stratum corneum.

REFERENCE SIGNS LIST 2 microneedle
4 fluid passage hole
5 transdermal administration device
8 needle support
10 holder
12 cap
14 elastic piece

The invention claimed is:

1. A transdermal administration device comprising:
a needle support with a plurality of microneedles formed at a tip portion thereof;
a holder with the needle support placed therein, allowing the needle support to protrude itself therefrom and retract itself therein;
a cap for covering the microneedles;
a spring member placed between the needle support and the holder, for biasing the needle support in a protruding direction;
an engaging portion formed at a base of the needle support; and
an engaged portion formed in the holder, capable of engaging the engaging portion,
wherein the engaging portion of the needle support can be engaged with the engaged portion of the holder when the needle support is retracted in the holder,
wherein the cap includes a retaining portion placed inside the cap, the retaining portion capable of retaining a medical fluid, and
wherein the cap includes a seal portion formed in a wall portion of the cap, the seal portion allowing a needle for providing the medical fluid to be inserted, and the needle penetrating through the seal portion can provide the medical fluid in the retaining portion.

2. The transdermal administration device according to claim 1, wherein the engaging portion formed at the base of the needle support is a protruded portion, the engaged portion formed in the holder is a through hole, and the protruded portion is engaged with the through hole.

3. The transdermal administration device according to claim 2, wherein the base of the needle support includes an elastic piece being extended therefrom, and the protruded portion is formed on an outer surface of the elastic piece.

4. The transdermal administration device according to claim 1, wherein the transdermal administration device is formed of biodegradable plastic.

5. The transdermal administration device according to claim 1, wherein the microneedle is formed of thermoplastic resin or metal, having a base diameter of Φ10 to 1000 μm, a tip diameter 10 to 1000 μm, and a height of 10 to 1500 μm.

6. The transdermal administration device according to claim 1, wherein the tip portion of the needle support is formed to be a planar or convex surface, and the plurality of microneedles are formed at the tip portion.

7. A transdermal administration device, comprising:
a needle support with a microneedle provided at a tip portion thereof;
a holder for holding the needle support movably;
a cap attached to the tip portion of the needle support to cover the microneedle;
a medical fluid storing portion formed at a tip portion of the needle support, the medical fluid storing portion being continuously connected to the microneedle;
a spring for biasing the needle support in a protruding direction is placed between the needle support and the holder; and
a plunger for sealing an opening of the medical fluid storing portion, the plunger located between the needle support and the holder, with a space between the plunger and the holder, wherein the holder includes a protruding portion, a proximal end of the plunger is received in a hole portion of the protruding portion, and the space between the plunger and the holder is located within the hole portion of the protruding portion.

8. The transdermal administration device according to claim 7, wherein the protruding portion is ring-shaped.

9. The transdermal administration device according to claim 7, wherein the holder includes an outer cylinder and an inner cylinder, and the protruding portion extends from a distal end of the inner cylinder.

10. A transdermal administration device, comprising:
a needle support with a microneedle provided at a tip portion thereof;
a holder for holding the needle support movably;
a cap attached to the tip portion of the needle support to cover the microneedle;
a medical fluid storing portion formed at a tip portion of the needle support, the medical fluid storing portion being continuously connected to the microneedle;
a spring for biasing the needle support in a protruding direction is placed between the needle support and the holder; and
a plunger for sealing an opening of the medical fluid storing portion, the plunger located between the needle support and the holder, with a space between the plunger and the holder, wherein the holder includes an outer cylinder and an inner cylinder, and a ring-shaped space portion is formed between the inner cylinder and the outer cylinder, and wherein the spring and the needle support are received in the ring-shaped space portion.

11. A transdermal administration device, comprising:
a needle support with a microneedle provided at a tip portion thereof;
a holder for holding the needle support movably;
a cap attached to the tip portion of the needle support to cover the microneedle;
a medical fluid storing portion formed at a tip portion of the needle support, the medical fluid storing portion being continuously connected to the microneedle;
a spring for biasing the needle support in a protruding direction is placed between the needle support and the holder; and a plunger for sealing an opening of the medical fluid storing portion, the plunger located between the needle support and the holder, with a space between the plunger and the holder, wherein the holder includes a receptacle portion that receives a proximal end of the plunger, the space between the plunger and the holder being located between the proximal end of the plunger and a base of the receptacle portion, and the base of the receptacle portion engaging the proximal end of the plunger to advance the plunger when the spring is compressed.

* * * * *